United States Patent [19]

Lee et al.

[11] Patent Number: 4,492,798
[45] Date of Patent: Jan. 8, 1985

[54] PROCESS FOR PREPARING ARYLALKYLPYRUVIC ACIDS

[75] Inventors: John Y. Lee; Joachim W. Wolfram, both of Baton Rouge, La.

[73] Assignee: Ethyl Corporation, Richmond, Va.

[21] Appl. No.: 457,520

[22] Filed: Jan. 13, 1983

Related U.S. Application Data

[63] Continuation-in-part of Ser. No. 353,440, Mar. 1, 1982, abandoned.

[51] Int. Cl.$^3$ .............................................. C07C 51/10
[52] U.S. Cl. ................................ 562/406; 260/465 D; 560/139; 560/145
[58] Field of Search ................... 562/406; 260/465 D; 560/139, 145

[56] References Cited

U.S. PATENT DOCUMENTS

| | | | |
|---|---|---|---|
| 3,116,306 | 12/1963 | Heck | 562/520 |
| 3,708,529 | 1/1973 | Cassar | 562/406 |
| 3,928,429 | 12/1975 | El-Chahawi | 562/406 |
| 4,128,572 | 12/1978 | Cassar | 562/406 |
| 4,152,352 | 5/1979 | Perron | 562/406 |

FOREIGN PATENT DOCUMENTS 2026478  2/1980  United Kingdom .

OTHER PUBLICATIONS

Chem. Abst: 95: 132511p (1981).
Francalanci Journal of Electroanalytical Chemistry, 232 pp. 59–70 (1982).

*Primary Examiner*—Michael L. Shippen
*Attorney, Agent, or Firm*—Donald L. Johnson; John F. Sieberth; John F. Hunt

[57] ABSTRACT

A process for the production of an arylalkylpyruvic acid of the general formula:

$$(R)_n-A-(CH_2)_m CH_2 COCOOH$$

wherein:
A represents an aromatic hydrocarbon radical containing 1 or 2 condensed benzene rings,
each R, which may be the same or different, represents hydrogen or a linear or branched alkyl radical with up to 4 carbon atoms which is unsubstituted or substituted by a nitro group or by an alkoxy group containing 1 to 4 carbon atoms, or an alkoxy group containing 1 to 4 carbon atoms, or a halogeno, nitrile, nitro or alkylcarbonyloxy group,
n is 0 or an integer from 1–3 when A contains one benzene ring, and n is 0 or an integer from 1–5 when A contains two condensed benzene rings and m is 1–20, which comprises carbonylating an arylalkyl halide of the general formula:

$$(R)_n-A-(CH_2)_m CH_2 X$$

where R, n, A and m are defined above and X represents halogen, by reacting the arylalkyl halide in a liquid solvent medium, with carbon monoxide at elevated temperature and pressure in the presence of a catalytic amount of a metal carbonyl compound and an alkali or an alkaline earth metal inorganic base.

27 Claims, No Drawings

PROCESS FOR PREPARING ARYLALKYLPYRUVIC ACIDS

REFERENCE TO RELATED APPLICATION

This is a continuation-in-part of prior co-pending application Ser. No. 353,440, filed Mar. 1, 1982, now abandoned.

BACKGROUND

The present invention relates to a process for the carbonylation of arylalkyl halides to form an arylalkylpyruvic acid as the predominant product. More particularly, the present invention relates to the carbonylation of an arylalkyl halide to form benzylpyruvic acid and other arylalkylpyruvic acids containing in the aromatic part of their molecules a benzene ring which may or may not be substituted or condensed benzene rings which also may or may not be substituted.

The practical value of such α-keto-carboxylic acids and their salts is that they play an important role in biochemistry. For example, they have been found to be useful as hypoglycemics.

It is known in the art to prepare arylpyruvic acids. Specifically pertinent to the process of the present invention is U.S. Pat. No. 4,152,352 which discloses the preparation of an arylpyruvic acid by reacting an arylmethyl halide in a liquid solvent medium with carbon monoxide at pressures of 5 to 200 bars in the presence of a catalytic amount of a metal carbonyl compound and an alkaline earth metal inorganic base. Also pertinent is U.K. patent application No. 2,026,478A, which discloses that alkali metal salts of an arylpyruvic acid can be prepared by reacting an arylmethyl halide, carbon monoxide and an alkali metal base in the presence of a metal carbonyl compound as catalyst and in the presence of an alcohol or cyclic ether as solvent.

While the art demonstrates that arylpyruvic acids can be made by reacting an arylmethyl halide with carbon monoxide in the presence of a carbonyl compound and a basic substance, it would be unexpected that less reactive arylalkyl halides having more than one methylene group attached to the aromatic moiety in their structure could be carbonylated under similar reaction conditions to form arylalkylpyruvic acids.

SUMMARY

It has now been found that an arylalkylpyruvic acid of the general formula:

$$(R)_n-A-(CH_2)_m CH_2 COCOOH$$

in which:

A represents an aromatic hydrocarbon radical containing 1 or 2 condensed benzene rings, and each R, which may be the same or different, represents hydrogen or a linear or branched alkyl radical with up to 4 carbon atoms which is unsubstituted or substituted by a nitro group or by an alkoxy group containing 1 to 4 carbon atoms, or an alkoxy group containing 1 to 4 carbon atoms or a halogeno, nitrile, nitro or alkylcarbonyloxy group, and n is 0 or an integer from 1-3 when A contains one benzene ring, and n is 0 or an integer from 1-5 when A contains two condensed benzene rings and m is 1-20, can be prepared in high yields by carbonylating an arylalkyl halide of the general formula:

$$(R)_n-A-(CH_2)_m CH_2 X \qquad (I)$$

where R, n, A and m are as defined above and X represents halogen, in a liquid solvent medium, with carbon monoxide at a pressure of from about 300 to 3000 psig in the presence of a catalytic amount of a metal carbonyl compound and an alkali or an alkaline earth metal inorganic base.

DESCRIPTION OF THE PREFERRED EMBODIMENTS

Specific examples of halides of the formula (I) which can be used in the present process include phenethyl bromide or chloride, 2-(o-methylphenyl)ethyl bromide or chloride, 2-(m-methylphenyl)ethyl bromide or chloride, 2-(p-methylphenyl)ethyl bromide or chloride, 2-(2',6'-dimethylphenyl)ethyl bromide or chloride, 2-(3',5'-dimethylphenyl)ethyl bromide or chloride, 2-(2',4'-dimethylphenyl)ethyl bromide or chloride, 2-(3',4'-dimethylphenyl)ethyl bromide or chloride, 2-(2',3'-dimethylphenyl)ethyl bromide or chloride, 2-(2',5'-dimethylphenyl)ethyl bromide or chloride, 1-(2'-bromoethyl)naphthalene and the like.

The reaction is carried out in the presence of a mixture of water and alcohol as a reaction medium in which the carbonylation of the arylalkyl halides takes place. Preferably, the alcohols employed for the reaction may be straight-chain, branched or cyclic, and preferably contain up to 6 carbon atoms. Methanol, ethanol, propanol, isopropanol, n-butanol, isobutanol, tert-butanol, and tert-amyl alcohol may be mentioned as examples. Cyclic ethers, such as tetrahydrofuran, also may be used. The particularly preferred solvent alcohol is tert-butanol. Mixtures containing about 10% to 90% by weight of water and about 90% to 10% by weight of alcohol generally are used. Preferred mixtures contain about 30% to 80% by weight water and about 70% to 20% by weight alcohol.

The reaction takes place in the presence of a basic substance suitably an alkali or an alkaline earth metal hydroxide employing a metal carbonyl compound. Although not wishing to be bound by theory, it is believed that the arylalkyl halide compound undergoes a reaction with the carbon monoxide and basic substance whereby the salt of the arylalkylpyruvic acid is formed from which the arylalkylpyruvic acid is isolated after acidification in a known manner.

Specific examples of suitable basic agents which can be used in the practice of the process include: LiOH, NaOH, KOH, RbOH, Ca(OH)$_2$, Ba(OH)$_2$ and Mg(OH)$_2$. LiOH and Ca(OH)$_2$ are particularly preferred. Yields of arylalkylpyruvic acids of up to approximately 90% can be obtained using Ca(OH)$_2$ as the basic substance and a solvent medium of tert.-butanol and water. Yields of up to approximately 74% of arylalkylpyruvic acid can be realized when LiOH is used as the basic agent in a tert.-butanol-water system.

The amount of basic agent used can vary within wide limits. In general, the molar ratio of the alkali metal or alkaline earth metal base to the arylalkyl halide is preferably 6:1 to 2:1.

In the process described herein, it is preferred to use metal carbonyl compounds as carbonylation catalysts. These catalysts include particularly metal carbonyls such as iron pentacarbonyl, dicobalt-octacarbonyl and nickel-tetracarbonyl, or their salts such as, for example, the potassium or sodium salts thereof. Dicobalt-octacarbonyl is very particularly suited. These catalysts can be added to the medium in the solid state or in the form of solutions in the solvent used for the carbonylation reaction. The weight ratio of the metal carbonyl compound to the arylalkyl halide is preferably from about 1:1 to 1:300 and more preferably from about 1:10 to 1:100.

The concentration of the arylalkyl halide of formula (I) used in the reaction solvent is not critical and can vary within wide limits. Thus, it can be between about 1 and 30% by weight, based on the weight of the solvent, however, it is possible to go outside of these limits without disadvantage.

The present process is advantageously carried out by bringing the mixture consisting of the arylalkyl halide, the metal carbonyl catalyst and the alkali or alkaline earth metal base, suspended in the mixture of water and alcohol, into contact, under nitrogen, in a suitable pressure-resistant reactor equipped with a stirrer, with a large excess of carbon monoxide (amount greater than 2 moles of carbon monoxide per mole of the arylalkyl halide) introduced at the desired pressure and temperature, in accordance with techniques suitable for bringing about the reaction between a liquid phase and a gas phase.

The carbonylation reaction is carried out at a temperature in the range of from about 30° C. to about 150° C., preferably from about 50° C. to 120° C., over a period of time of from about 3 to 60 hours, typically 3 to 20 hours.

In general, the reaction takes place at elevated carbon monoxide pressures. Typical elevated pressures are those pressures falling in the range of from about 300 psig to about 3000 psig. Preferably, the reaction takes place at a pressure in the range of about 300 psig to 1000 psig. The carbon monoxide may contain or be mixed with an inert gas, such as nitrogen.

On completion of the reaction, the product mixture is filtered, resulting in the alkali metal or alkaline earth metal salt of the arylalkylpyruvic acid being separated from the liquid reaction components as the main solid component, together with a small amount of the alkali metal or alkaline earth metal salt of the arylalkylacetic acid in solid form. The filtrate contains the remainder of the alkali or alkaline earth metal salt of the arylakylacetic acid, and, where unbranched alcohols are used, also esters in addition to very small quantities of the salt of the arylalkylpyruvic acid, unreacted arylalkyl halide and arylalkyl alcohol.

In a further process step, the metal salt of the arylalkylpyruvic acid is acidified with a dilute acid, such as hydrochloric acid, so as to displace the arylalkylpyruvic acid from its alkali or alkaline earth metal salt. The solution obtained is extracted with a suitable solvent, for example, an ether such as diethyl ether, and the organic extract thus obtained is purified by conventional acid-base work-up. The final residue consists of very pure arylalkylpyruvic acid.

The reaction filtrate can be treated, if desired to recover the arylalkylacetic acid which it contains. For example, it is possible to free it from the water and the alcohol and, where appropriate, from the unreacted arylalkyl halide which it contains by distillation at atmospheric pressure. After cooling, the mixture can be acidified with an inorganic acid such as HCl and the mixture subsequently extracted with a suitable solvent, for example diethyl ether. The organic extract is then washed with an aqueous alkaline solution and the aqueous wash solution acidified and extracted to give, after removing the extraction solvent, a residual mixture containing the arylalkylacetic acid.

If desired, lower alkyl esters of the arylalkylpyruvic acid products of the present invention can be prepared by esterifying the arylalkylpyruvic acid product according to conventional esterification techniques employing lower aliphatic alkanol in the presence of acid catalysts such as, for example, $BF_3$, $BF_3.HCl$, or $BF_3.MeOH$, $BF_3.Et_2O$ or diazomethane at suitable reaction conditions.

Experiments have shown that certain reaction conditions and components give better yields of the desired salts and acids than others. Optimum yields range from about 50% to about 90%. The reaction appears most facile at CO pressures of approximately 300–900 psig and at temperatures of from about 30° C. to 120° C. The chelating ability and size of the base cation, the stability and the solubility of the particular base in the solvent, temperature and CO pressure all appear to influence the reaction rate and product distribution. LiOH is the most reactive base followed by $Ca(OH)_2$ and NaOH.

The highest yield of arylalkylpyruvic acid which was obtained by the process of the invention was approximately 90%. This was obtained using $Ca(OH)_2$ in a tertiary butanol-water solvent medium at a reaction temperature of approximately 84° C. and a pressure of about 900 psig.

The following examples illustrate the invention.

EXAMPLE 1

9.25 g (50 mmoles) of phenethyl bromide, 30 ml of t-BuOH, 700 mg (~2 mmoles) of $Co_2(CO)_8$, 80 ml of $H_2O$, 4.8 g (200 mmoles) of LiOH were stirred in a 300 ml autoclave for 24 hours at 70° C. and under 300 psig CO pressure. The reaction mixture was cooled to room temperature, then filtered. The crude cake was rinsed with 20 ml of $Et_2O$ to give a pale yellow solid, which was acidified in cooled HCl solution (check by pH paper) and extracted with $Et_2O$. The neutral impurities in the filtrate were extracted with $Et_2O$ and discarded; any acidic material left in the acidified filtrate (pH=2 by adding HCl) was extracted with $Et_2O$ (3×30 ml). Approximately 74% isolated yield of benzylpyruvic acid identified by both $^1H$ NMR and $^{13}C$ NMR was obtained from the combined $Et_2O$ solution.

EXAMPLE 2

Under 900 psig CO pressure after 15 hours reaction, 9.3 g (50 mmoles) of phenethyl bromide, 10 g (130 mmmoles) of $Ca(OH)_2$, 30 ml t-BuOH, 80 ml $H_2O$, 700 mg (2 mmoles) of $Co_2(CO)_8$ were stirred in a 300 ml autoclave at 84° C. Then the reaction mixture was cooled and filtered. The calcium salt of benzylpyruvic acid was acidified with excess HCl and extracted with $Et_2O$ (2×120 ml) to give ~90% isolated yield of benzylpyruvic acid.

EXAMPLE 3

90 mg (0.5 mmoles) of benzylpyruvic acid obtained by the procedure set forth in Example 1, 150 mg (1.1 mmoles) of $BF_3.Et_2O$ in 5 ml of EtOH were stirred in a 25 ml flask at reflux temperature for 130 minutes. The reaction mixture was evaporated to oily residue. Then 25 ml of $CH_2Cl_2$ was added; the organic solution was washed with $H_2O$ (3×15 ml), dried over $MgSO_4$ and evaporated to give 64% (GC area %) yield of benzylpyruvic acid ester ($^1H$ NMR and $^{13}C$ NMR).

In a similar manner, several other examples of the present invention were carried out. The results of such experiments using varying conditions of reaction and different reactants are given in the following table.

TABLE

Preparation Of Benzylpyruvic Acid By Reaction Of Phenethyl Bromide With Carbon Monoxide in the Presence of Metal Carbonyl, Base and Solvent

| Example No. | Phenethyl Bromide (mmoles) | Base/ mmoles | Solvent ml | $Co_2(CO)_8$ (mmoles) | CO (psig) | Temp. (0° C.) | Time (hours) | Benzylpyruvic Acid Yield |
|---|---|---|---|---|---|---|---|---|
| 4 | 50 | LiOH (200) | t-BuOH (30) $H_2O$ (80) | ~2 | 300 | 70 | 24 | 50% |
| 5 | 50 | LiOH (200) | t-BuOH (30) $H_2O$ (50) | ~2 | 300 | 70 | 20 | 66% |
| 6 | 50 | NaOH (200) | t-BuOH (30) $H_2O$ (80) | ~2 | 300 | 70 | 60 | 16% |
| 7 | 50 | LiOH (100) | t-BuOH (30) $H_2O$ (80) | ~2 | 300 | 80 | 17 | 20% |
| 8 | 50 | LiOH (200) | t-BuOH (30) $H_2O$ (80) | ~2 | 300 | 90-100 | 3 | 57% (salt) |
| 9 | 50 | LiOH (150) | t-BuOH (30) $H_2O$ (80) | ~2 | 300 | 90-100 | 3 | 38% (salt) |
| 10 | 50 | $Ca(OH)_2$ (100) | t-BuOH (30) $H_2O$ (80) | ~2 | 300 | 90 | 24 | 0% |
| 11 | 50 | NaOH (250) | t-BuOH (50) $H_2O$ (110) | ~2 | 950 | 60 | 20 | trace |
| 12 | 50 | NaOH (250) | t-BuOH (50) $H_2O$ (110) | ~2 | 900 | 90 | 20 | 0% |
| 13 | 25 | LiOH (100) | t-BuOH (30) $H_2O$ (80) | ~2 | 950 | 70 | 4 | 35% |
| 14 | 50 | LiOH (200) | t-BuOH (30) $H_2O$ (80) | ~2 | 950 | 80-90 | 3 | 47% (salt) |
| 15 | 50 | $Ca(OH)_2$ (130) | t-BuOH (30) $H_2O$ (80) | ~2 | 900 | 96 | 60 | 77% |
| 16 | 50 | $Ca(OH)_2$ (130) | t-BuOH (30) $H_2O$ (80) | ~2 | 600 | 84 | 24 | 66% |
| 17 | 50 | $Ca(OH)_2$ (130) | t-BuOH (30) $H_2O$ (80) | ~2 | 540 | 96 | 8 | 67.4% |

A comparison between Example No. 7 and Example No. 5 in the table indicates that at approximately the same reaction conditions a reduction in the amount of LiOH used in the reaction has an adverse effect on the yield of benzylpyruvic acid by reducing the yield from about 66% in Example No. 5 to about 20% in Example No. 7. Reference to Example No. 6 indicates that NaOH is a less reactive base than either LiOH or $Ca(OH)_2$ affording only a 16% yield of benzylpyruvic acid. A comparison between Example No. 10 and Example No. 15 demonstrates the effect a reduction in pressure has on the yield of benzylpyruvic acid when $Ca(OH)_2$ is used as the basic agent. At similar reaction conditions, the yield of acid dropped from approximately 77% in Example No. 15 (900 psig) to 0% in Example No. 10 (300 psig). The lack of product in Example Nos. 11 and 12 cannot be explained other than to say a lack of product was not consistent with the overall results obtained and might perhaps be attributed to leakage in the reaction system.

Having described the process which Applicant regards as his invention, it should be recognized that changes and variations within the scope and spirit of the invention can be made by one skilled in the art and it is accordingly to be understood that the present description of the invention is illustrative only. It is desired that the invention be limited only by the lawful scope of the following claims.

We claim:

1. A process for the production of an arylalkylpyruvic acid of the general formula:

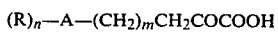

$(R)_n$—A—$(CH_2)_m CH_2 COCOOH$ or a salt thereof wherein:

A represents a benzene or naphthalene group,
each R, which may be the same or different, represents hydrogen or a linear or branched alkyl radical with up to 4 carbon atoms which is unsubstituted or substituted by a nitro group or by an alkoxy group containing 1 to 4 carbon atoms, or an alkoxy group containing 1 to 4 carbon atoms, or a halogeno, nitrile, nitro or alkylcarbonyloxy group,
n is 0 or an integer from 1–3 when A is a benzene group, and n is 0 or an integer from 1–5 when A is a naphthalene group and m is 1-20, which comprises carbonylating an arylalkyl halide of the general formula:

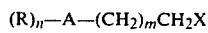

$(R)_n$—A—$(CH_2)_m CH_2 X$ where R, n, A and m are defined above and X represents halogen, by reacting the arylalkyl halide in a liquid solvent medium of a mixture of water and alcohol, with carbon monoxide at elevated temperature and pressure in the presence of a catalytic amount of a metal carbonyl compound wherein said metal is iron, nickel, or cobalt and an alkali or an alkaline earth metal inorganic base to form a salt of the arylalkylpyruvic acid, and optionally then acidifying the salt to form said acid.

2. A process according to claim 1, wherein R represents a methyl or ethyl group, or fluorine, chlorine, bromine or iodine, and n is 0 or 1 or 2 when A represents a benzene ring, and is 0,1,2 or 3 when A represents a naphthalene group, and x represents chlorine or bromine.

3. A process according to claim 1, wherein the arylalkyl halide is phenethyl bromide or chloride, 2-(o-methylphenyl)ethyl bromide or chloride, 2-(m-methylphenyl)ethyl bromide or chloride, 2-(p-methylphenyl)ethyl bromide or chloride, 2-(2',6'-dimethylphenyl)ethyl bromide or chloride, 2-(3',5'-dimethylphenyl- )ethyl bromide or chloride, 2-(2′,4′-dimethylphenyl-
)ethyl bromide or chloride, 2-(3′,4′-dimethylphenyl-
)ethyl bromide or chloride, 2-(2′,3′-dimethylphenyl-
)ethyl bromide or chloride, 2-(2′,5′-dimethylphenyl-
)ethyl bromide or chloride, 1-(2′-bromoethyl)naphthalene.

4. A process according to claim 1, wherein the carbon monoxide pressure is from about 300 to 3000 psig.

5. A process according to claim 1, wherein the reaction is carried out at a temperature of from about 30° C. to about 150° C.

6. A process according to claim 1, wherein the inorganic base is selected from LiOH, NaOH, KOH, RbOH, Ca(OH)$_2$, Ba(OH)$_2$ or Mg(OH)$_2$.

7. A process according to claim 1, wherein the molar ratio of the inorganic base is from about 2 to 6 moles per mole of arylalkyl halide.

8. A process according to claim 1, wherein the metal carbonyl catalyst compound is iron pentacarbonyl, dicobalt-octacarbonyl, or nickel-tetracarbonyl.

9. A process according to claim 8, wherein the metal carbonyl is dicobalt-octacarbonyl.

10. A process according to claim 8, wherein the metal carbonyl catalyst compound is a salt of iron pentacarbonyl, dicobalt-octacarbonyl or nickel-tetracarbonyl.

11. A process according to claim 10, wherein said salt is sodium or potassium.

12. A process according to claim 1, wherein the weight ratio of the metal carbonyl compound to the arylalkyl halide is from about 1:1 to 1:300.

13. A process according to claim 1, wherein the water and alcohol mixture consists of from about 10% to about 90% by weight water and from about 90% to about 10% alcohol.

14. A process according to claim 1, wherein the alcohol is a saturated, linear or branched, aliphatic, monohydroxylic or polyhydroxylic compound containing up to 6 carbon atoms.

15. A process according to claim 14, wherein the alcohol is tert.-butanol.

16. The process of claim 1 for the production of an arylalkylpyruvic acid wherein the salt of the arylalkylpyruvic acid is acidified to form said arylalkylpyruvic acid.

17. A process for the production of an arylalkylpyruvic acid of the general formula:

(R)$_n$—A—(CH$_2$)$_m$CH$_2$COCOOH or a salt thereof wherein:
A represents a benzene or naphthalene group, each R, which may be the same or different, represents hydrogen or a linear or branched alkyl radical with up to 4 carbon atoms which is unsubstituted or substituted by a nitro group or by an alkoxy group containing 1 to 4 carbon atoms or an alkoxy group containing 1 to 4 carbon atoms or a halogeno, nitrile, nitro, or alkylcarbonyloxy group, n is 0 or an integer from 1–3 when A is a benzene group and n is 0 or an integer from 1–5 when A is a naphthalene group and m is 1–20, which comprises carbonylating an arylalkyl halide of the general formula:

(R)$_n$—A—(CH$_2$)$_m$CH$_2$X where R, n, A, and m are as defined above and X represents halogen, by reacting about 1 mole part of the arylalkyl halide in a liquid solvent medium of a mixture of water and alcohol, with carbon monoxide at elevated temperature and pressure in the presence of a catalytic amount of a metal carbonyl compound selected from iron, cobalt, and nickel compounds, and at least about 2 mole parts of an alkaline earth metal inorganic base or at least about 4 mole parts of an alkali metal inorganic base so as to form a salt of the arylalkylpyruvic acid, and optionally then acidifying the salt to form said arylalkylpyruvic acid.

18. The process of claim 17 wherein the catalyst is dicobaltoctacarbonyl, Co$_2$(CO)$_8$.

19. The process of claim 17 carried out in the presence of an alkali metal inorganic base comprising LiOH.

20. The process of claim 17 carried out in the presence of an alkaline earth metal inorganic base comprising calcium hydroxide, Ca(OH)$_2$.

21. The process of claim 17 carried out at at least about 90° C.

22. The process of claim 17 carried out for at least about 8 hours.

23. The process of claim 21 carried out for at least about 8 hours.

24. The process of claim 17 wherein A is a benzene group, n=0, and m=1 or 2.

25. The process of claim 17 for the production of an arylalkylpyruvic acid wherein said salt is acidified to form said arylalkylpyruvic acid.

26. A process for the production of an arylalkylpyruvic acid of the general formula:

A—(CH$_2$)$_m$CH$_2$COOOH or a salt thereof wherein:
A represents a naphthalene group and m is 1–20, which process comprises carbonylating an arylalkyl halide of the general formula, A—(CH$_2$)$_m$CH$_2$X where A and m are as defined above and X represents chlorine or bromine, by reacting 1 mole part of the arylalkyl halide in a liquid solvent medium of a mixture of water and alcohol, with carbon monoxide at at least about 300 psig and at least about 70° C. in the presence of a catalytic amount of a metal carbonyl compound selected from iron carbonyls, cobalt carbonyls, and nickel carbonyls and also in the presence of at least about 4 mole parts of an alkali metal hydroxide or at least about 2 mole parts of an alkaline earth metal hydroxide so as to form a salt of the arylalkylpyruvic acid, and then optionally acidifying the salt to form said arylalkylpyruvic acid.

27. The process of claim 24 for the production of an arylalkylpyruvic acid wherein said salt is acidified to form said arylalkylpyruvic acid.

* * * * *

UNITED STATES PATENT AND TRADEMARK OFFICE
CERTIFICATE OF CORRECTION

PATENT NO.   :  4,492,798

DATED        :  JANUARY 8, 1985

INVENTOR(S)  :  JOHN Y. LEE and JOACHIM W. WOLFRAM

It is certified that error appears in the above-identified patent and that said Letters Patent is hereby corrected as shown below:

Column 2, line 30, reads "6carbon" and should read -- 6 carbon --.

Column 4, line 51, reads "(130 mmmoles)" and should read -- (130 mmoles) --.

Column 8, line 59, reads "claim 24" and should read -- claim 26 --.

Signed and Sealed this

Twenty-fifth Day of June 1985

[SEAL]

Attest:

DONALD J. QUIGG

Attesting Officer     Acting Commissioner of Patents and Trademarks